United States Patent
Garrett (10) Patent No.: US 6,542,231 B1
(45) Date of Patent: Apr. 1, 2003

(54) FIBER-COUPLED LIQUID SAMPLE ANALYZER WITH LIQUID FLOW CELL

(75) Inventor: Mark H. Garrett, Morgan Hill, CA (US)

(73) Assignee: Thermo Finnegan LLC, San Jose, CA (US)

( * ) Notice: Subject to any disclaimer, the term of this patent is extended or adjusted under 35 U.S.C. 154(b) by 154 days.

(21) Appl. No.: 09/644,194

(22) Filed: Aug. 22, 2000

(51) Int. Cl.[7] .................................................. G01N 7/10
(52) U.S. Cl. ..................... 356/246; 356/244; 385/12; 385/125; 250/227.11; 250/295.95
(58) Field of Search ................... 356/246, 244, 356/317, 318, 344; 250/227.25, 227.11, 225.25, 343; 385/12, 125, 141, 143, 145, 28

(56) References Cited

U.S. PATENT DOCUMENTS

| | | | |
|---|---|---|---|
| 3,641,332 A | * 2/1972 | Reick et al. | 350/96 R |
| 3,954,341 A | 5/1976 | Uffenheimer | 356/181 |
| 4,575,424 A | 3/1986 | Allington et al. | 210/198.2 |
| 4,867,559 A | 9/1989 | Bach | 356/73 |
| 4,989,974 A | * 2/1991 | Anton et al. | 356/246 |
| 5,140,169 A | 8/1992 | Evens et al. | |
| 5,170,056 A | * 12/1992 | Berard et al. | 250/341 |
| 5,184,192 A | 2/1993 | Gilby et al. | |
| 5,194,915 A | 3/1993 | Gilby | 356/318 |
| 5,312,535 A | * 5/1994 | Waska et al. | 356/344 |
| 5,327,225 A | * 7/1994 | Bender et al. | 356/318 |
| 5,412,750 A | 5/1995 | Nath | 385/125 |
| 5,416,879 A | 5/1995 | Liu | 385/125 |
| 5,423,513 A | 6/1995 | Chervet et al. | 250/227.25 |
| 5,444,807 A | 8/1995 | Liu | |
| 5,570,447 A | 10/1996 | Liu | 385/125 |
| 5,608,517 A | 3/1997 | Munk | 356/246 |
| 5,714,388 A | 2/1998 | Kusnetz | 436/172 |
| 5,952,035 A | * 9/1999 | Erb et al. | 427/2.11 |
| 6,108,083 A | * 8/2000 | Machler | 356/246 |
| 6,188,813 B1 | * 2/2001 | Dourdeville et al. | 385/12 |

FOREIGN PATENT DOCUMENTS

EP        0814332 A2      12/1997

OTHER PUBLICATIONS

Altkorn, Robert et al., "Waveguide Capillary Cell for Low–Refractive–Index Liquids", *Applied Spectroscopy*, vol. 51, No. 10, 1997, pp. 1154–1158.

* cited by examiner

Primary Examiner—Frank G. Font
Assistant Examiner—Sang H. Nguyen (57) ABSTRACT

A liquid sample analyzer with a flow-through liquid waveguide cell is described. The light source is fiber coupled to a liquid waveguide or light pipe. The light pipe can be remotely located and fiber coupled to the spectrometer so that the light source is thermally isolated making the spectrometer easily thermally stabilized, and the dispersion minimized. The liquid waveguide cell includes a light pipe that has a lower index of refraction than the liquid flowing through the light pipe. Light is input into the liquid waveguide by an optical fiber that is coupled to the liquid waveguide. The optical fiber diameter and the light pipe core diameter and spacing are selected to provide coupling of all light modes transmitted through the optical fiber into the light pipe. The output light is received by an optical fiber which is arranged to receive all of the light transmitted through the light pipe. The light output from the light pipe is fiber-coupled to the spectrometer with a fiber bundle that is arranged in the form of a slit at the distal end or entrance aperture of the spectrometer.

29 Claims, 7 Drawing Sheets

FIG_1

FIG_2

FIG_3

FIG_4

FIG_5

FIG_6

FIG_7

FIG_8

FIBER-COUPLED LIQUID SAMPLE ANALYZER WITH LIQUID FLOW CELL

BRIEF DESCRIPTION OF THE INVENTION

This invention relates to a fiber-coupled liquid sample analyzer with a liquid flow cell that guides light by total internal reflection (called a light pipe), and more particularly to an analyzer used for light absorption measurements that are typically made in high performance liquid chromatography (HPLC), capillary liquid chromatography ($\mu$LC), capillary electrophoresis (CE), capillary electrochromatography (CEC), super critical liquid chromatography (SFC), flow injection analysis (FIA) and related techniques.

BACKGROUND OF THE INVENTION

Liquid chromatography is a widely accepted method of determining the absorbence of substances and their concentrations. The absorbence of a solution is determined according to Beer's Law:

$$A = \epsilon b c = \log(1/T) = \log(P_0/P)$$

The symbol "A" represents the solution absorbence, "$\epsilon$" is the molar absorptivity, "c" is the concentration, "b" is the path length, "T" is the transmission, "$P_0$" is the incident light power, and "P" is the transmitted light power. Depending on the type of chromatography, e.g., CE compared to HPLC, there can be slightly different system design criteria and functional requirements. However, in general, all absorbence measurement systems for the various forms of liquid chromatography desire several common performance characteristics including (1) high sensitivity or a large signal-to-noise ratio (S/N) so as to observe low concentrations of an analyte, (2) low dispersion so as to maintain resolution between all analytes eluting from the separation media, and simultaneously, (3) a large linear dynamic range so that high and low concentrations can be determined with a single calibration of the absorbence.

Typically, HPLC systems with $10^4$ to $10^5$ linear dynamic range can measure less than one hundred micro AU (absorbence units) of absorbence. Noise levels are at about 20–40 micro AU. The resolution, on the other hand, is affected by the performance of the separation column and dispersion within the system. The chromatographer specifies the column depending on the materials to be analyzed. The other factor affecting resolution is dispersion. Compounds separated by the column pass through the detector. A plot of absorbence as a function of time will give a fairly Gaussian-shaped peak. Dispersion of the analyte within the solvent causes chromatographic peaks to broaden, reducing the absorbence signal. In addition, the distance between the borders of two peaks can become overlapped. Therefore, it is important to keep dispersion to an absolute minimum.

In general, fast separations using high flow rates are desired to reduce data acquisition times. However, this can also reduce the chromatographic resolution. Thus, in some instances, it is better to reduce the amount of analyte and reduce the flow rate. In that vein, chromatography has continued to reduce the volumes and flow rates, particularly in the area of Proteomics, or protein separation and quantification. Further, this is attractive where only small samples are available.

From a system point of view, to achieve high sensitivity and resolution, it is necessary to increase the signal as well as decrease the noise. A longer path length flow cell equates to a larger absorbence signal for a given sample concentration. Further, a longer path length implies that a lower concentration solution can be measured with equivalent incident light power, thus increasing the sensitivity of a HPLC method. Measuring lower concentrations is important for high purity drug synthesis, purity analysis, and chemical quality control.

In most instances, when achieving higher sensitivity, commercial absorbence measurement systems sacrifice dynamic range or vice versa. Noise sources, which affect the detection of absorbence changes, include short term and long-term noise sources. Short term noise arise from pressure induced index changes, light power fluctuations, electronic noise from the sensor and sensor electronics, fluctuations of light scattering from optical components such as lenses, mirrors, or gratings, high frequency jitter in the opto-mechanical components that cause the spectrum to move back and forth across the pixels of the array sensor, and background optical noise from external sources. Long-term noise arise from temperature fluctuations that cause optical alignments and coupling to vary, thermo-mechanical drift of the optical components, uncompensated drift in the detection electronics, and baseline shifts from the refractive index sensitivity of the flow cell. Clearly, the longer the path from the separation column to the flow cell the greater the dispersion resulting in a lower signal amplitude, broader signal, and lower resolution. Obviously, increasing the signal through a longer path flow cell is of no consequence if an offsetting increase in noise is simultaneously obtained.

Enhancement of the absorbence signal is clearly obtained with a longer path length flow cell that has low RI (refractive index) sensitivity, which results in drift of the baseline absorbence. The absorbence signal is further increased if the flow cell or light pipe is located near the separation column reducing the dispersion. Short-term noise caused by pressure induced index changes is typically reduced by flow restriction or pulse damping apparatus. Long-term noise from temperature drift is reduced by passive or active thermal control. The former case is usually the most cost effective, if it can be implemented. Matched diodes are usually used to obtain a signal and reference with equivalent drift that is subtracted out. Cooling sensors are often used in high sensitivity systems but results in added cost and complexity that is usually prohibited in a standard HPLC system. Often, in HPLC systems light sources must be judiciously isolated from the polychrometer to minimize thermally induced drift of the optical components. In most instances, the polychrometer is designed with costly materials and/or tight tolerances to account for these thermo-mechanical issues.

Normally, LC detector systems are made with bulk optics, that is, macro-scale lens, mirrors, and gratings where the light is transmitted between these components through free space. For instance, see U.S. Pat. Nos. 4,375,163, 4,848,904, 4,568,185, 5,495,186, 4,687,917, and 4,637,041. Generally, the light sources, relay optics, and spectrometer are integrated into a monolithic "optical bench". Alternatively, it is possible to transmit the light through optical fibers. This approach is attractive for several reasons that will be discussed herein. Fiber-optic absorbence systems are commercially available from Ocean Optics, Inc., Dunedin, Fla., and from Carl Zeiss, Jena, Germany. (See U.S. Pat. No. 5,159,404) However, these systems are not suitable for the HPLC applications described herein since they lack the dynamic range, they are typically less than $10^4$ AU's, and/or do not operate with a single grating over the desired spectral bandwidth, which is 190–800 nm for HPLC. In addition, the absorbence cells available with such systems are not designed with the functional, and performance needs of modern HPLC. What is critical to HPLC and other LC applications to obtain high dynamic range, sensitivity, and resolution is the system integration. There is interplay between all the components of the system including the pump, degasser, autosampler, injector valves, column, flow cell, spectrometer, and electronics that must be optimized.

It was previously difficult to use fiber optics in HPLC systems because the fiber would solarize or photo-darken when illuminated with ultra-violet (UV) light. Recently, "non-solarizing" silica-based fiber has become available in the form of high-OH fiber. In this fiber, OH is in-diffused during the fabrication and compensates defects of the fiber that lead to solarization. However, the OH also out-diffuses over time and thus solarization reappears. Heraeus-Amersil, Germany has developed a new non-solarizing preform for silica-based optical fibers that retains its UV transmission for much longer periods. This fiber, called UVM, is available through Polymicro Technologies, Phoenix, Ariz. Other combinations of UVM and High-OH are also available.

Given the present availability of stable, non-solarizing optical fiber it is now possible to conceive of fiber-coupled LC systems that will address some of the limitations of bulk-optic free space LC systems. Fiber coupling also removes the need for highly tolerance mechanical components since the tolerances for optical alignment are obtained with mass fabricated fiber optic connectors. These connectors are widely available at a low cost and can align optical fiber connections within microns yielding optical losses of less than 0.3 dB per connection.

In prior LC systems, the flow cell is illuminated by bulk optical components, and has been separated from the column by many centimeters of tubing resulting in a significant amount of "dead volume". The dead volume is the flow volume where the analyte can disperse into the solvent. A fiber-coupled light pipe would allow one to remotely locate the light pipe from the spectrometer and in close proximity or directly attached to the column. This means that the dead volume is minimized. Obviously, this will increase the signal strength increasing the sensitivity, and reduce peak broadening yielding higher resolution. This is particularly important to Proteomics, where micro liter and sub micro liter small sample volumes are available (micro-liters or less) and their dispersion would make them un-measurable. In addition without dispersion the peak height is maximized and long bore low volume light pipes permit high sensitivity.

Furthermore, fiber-coupling the light pipe means that it can be removed from the optical bench and placed where it is easily thermally stabilized, unaffected by the heat from the light sources of the system. In addition, the light source itself can be remotely located from the optical bench and thus the heat from the light source is not transmitted into the optical bench. This is especially important since it will reduce the thermo-mechanical tolerances of the spectrometer and reduce the size of the optical bench. In turn, the cost of the optical bench is greatly reduced and the system fabrication is simplified. Components are simply connected together with low-cost fiber optic connectors and receptacles widely available. A fiber-coupled system allows the elements of the system, for instance the light pipe, to be easily changed to optimize a particular analysis. For example, a long path length and/or low volume light pipe could be connected into the system when the particular analysis demands it. In addition, optical filters can be added in or taken or out of the system when needed.

Liquid chromatography (LC) is typically used to analyze sample volumes around 10 $\mu$L. Smaller sample volumes such as 3–5 nano liters are desirable for micro-column techniques. Current LC flow cell dimensions, about 1 cm in length with ±10 $\mu$L volumes, are limited in cross-section, and thus path length, by the need to avoid light interaction with the light-absorbing, typically metallic flow cell wall. If the path length of a typical flow cell is increased then the diameter and light entrance aperture must be reduced to maintain an equivalent volume. However, focusing an extended light source to a smaller spot size decreases the Rayleigh range, or waist of the light, which results in the light quickly refracting into the cell walls creating false absorbence and noise. Alternatively, given the same light source, a longer Rayleigh range decreases the power density. In accordance with Beer's law, a lower power density leads to a lower absorbence signal. Fundamentally, the second law of thermodynamics cannot be violated which applies here and is embodied in the law of conservation of luminance or radiance, or the LaGrange invariant.

In U.S. Pat. No. 3,954,341 Uffenheimer discusses a liquid sample analyzer with improved optical characteristics, in which a light conduit is described with a tubular wall with its index of refraction less than that of the flowing solution. In this light waveguide or light pipe, a smaller aperture requiring a smaller illumination spot size and concomitant smaller Rayleigh range is accommodated by a non-absorbing interaction with cell walls that reflects the light into the cell, called total internal reflection (TIR).

It is known that the light pipe (cladding) of a liquid waveguide needs to be made of a material with an index of refraction that is less than the index of the sample solution or analyte that is the core of the guide ($n_{clad}<n_{core}$). Typical analytes used in HPLC are low concentration water solutions (n=1.333), methanol solutions (n=1.328), or acetonitrile solutions (n=1.344). U.S. Pat. No. 4,867,559 describes a liquid-clad liquid waveguide for absorbence measurements where total internal reflection (TIR) is used for light guiding. Tsunoda et al. discusses the use of Teflon cladding (PTFE and FEP) for a TIR liquid waveguide in Applied Spectroscopy 163, 1990. U.S. Pat. No. 5,184,192 describes a TIR liquid-clad flow cell for fluorescence measurements.

The present invention teaches using Teflon AF, a better material for a light pipe, due to its relatively lower index of refraction (e.g., n=1.294), high transparency, and low scattering. Teflon AF is the trade name for copolymers of 2,2-bistrifluoromethyl-4,5-difluoro-1,3-dioxole (PDD) with TFE tetrafluoroethylene copolymers. A range of compositions and properties exist depending on the proportion of PDD. This is described in W. H. Buck, and P. R. Resnik, "Properties of Amorphous Fluoropolymers Based on 2,2-Bistrifluoromethyl-4,5-Difluoro-1,3-Dioxole," presented at the 183$^{rd}$ Meeting of the Electrochemical Society, Honolulu, Hi., May 17, 1993. Teflon AF has the lowest index of refraction of available Teflons. Teflon AF also has amorphous optical properties giving it low optical scattering compared to other Teflons including FEP, PFA and PTFE. U.S. Pat. Nos. 5,194,192 and 5,608,517 describe the design and fabrication of liquid waveguides with a Teflon AF cladding. Present production methods typically used for plastics are now available for Teflon AF including pulling from a preform, or an extrusion process to fabricate capillaries. Due to the high tensile strength of Teflon AF, thin wall, high-pressure capillaries or tubing are available for HPLC applications. Absorbence measurements using an unclad extruded Teflon AF 2400 are described by R. Altkorn, I. Koev, and A. Gottleib in, "Waveguide Capillary Cell for Low-Refractive-Index Liquids," Applied Spectroscopy, Vol. 51, No. 10, 1554 (1997). They discuss coupling into the liquid waveguide using standard PEEK (polyetheretherketone) LC tees and optical fibers inserted into the tee and into the Teflon AF waveguide. However, no consideration is given to the optimum light launching conditions, coupling design considerations, or light collection conditions to optimize the detection sensitivity. Nor do they offer conditions to minimize the refractive index (RI) sensitivity. They give no consideration to the numerical aperture (NA) of the output fiber and/or the modes within the guide. For instance, when the Teflon AF is bent, mode mixing will occur. Therefore, even if lower order modes of the waveguide are launched by the input fiber, higher order modes will propagate within the liquid waveguide. These modes will not be accepted by an output fiber that has the same NA as the input fiber. Cladding modes may also be induced with bending and these can be coupled into a larger diameter output fiber as a noise source. Consideration is not given to the RI sensitivity that can be incurred with a flexible, curved waveguide where bending losses will vary depending on selection of solvent. In addition, no cell design considerations are given with respect to the sensitivity of RI due to pressure. Further, compression fittings are used around the optical fibers which can increase the optical loss. Compression fittings are also used around the Teflon AF liquid waveguide that can similarly constrict light propagation. In the latter case, high pressure operation is precluded unless, rigid, large diameter Teflon AF is used or some external supporting tube is applied around the Teflon AF liquid waveguide so as to withstand the compression from the ferrule seal. As described in Xiaobing Xi and Edward S. Yeung, Appl. Spectro., 45, 7, 1199 (1991), compression around Teflon is shown to cause disruption in the optical waveguide. Finally, no consideration is given to the temperature sensitivity or the long-term drift of the absorbence of an exposed Teflon AF liquid waveguide.

Reduced analyte volumes can result in improved analysis due to shorter analysis times and reduced analysis costs. Micro-column liquid chromatography ($\mu$LC) and capillary electrophoresis (CE) systems have cell volumes on the order of 3–15 nano-liters with cross sections of 25 to 100 micrometers. Previous micro-designs used transparent micro-capillaries where the light is transmitted orthogonal to the fluid flow. This design greatly reduces the length over which the light interacts with the analyte. Short interaction lengths make high detection sensitivity difficult to obtain, according to Beer's law. Further, it is difficult to scale down a standard liquid chromatography cell to the necessary $\mu$LC dimensions. In addition, the smaller the light input cross-section the faster the light must be focused resulting in light that rapidly diverges from the focal point and is absorbed and scattered by the wall of the flow cell.

Liquid chromatography is performed with both isocratic and gradient solvent conditions. During elution, the concentration of the analyte varies over a time interval resulting in an absorbence change that is roughly Gaussian in shape. The total absorbence is equal to the area under the absorbence curve. The accuracy of the calculated absorbence is determined by the accuracy of the calculated integral of the absorbence curve. If the background absorbence changes during the absorbence measurement, the area under the curve becomes a less accurate measure of the absorbence. It is therefore desirable that the background absorbence be as stable as possible. In standard flow cells, baseline changes are due to index of refraction changes that occur during the elution. The typical sources of baseline drift are from Fresnel reflection, refraction induced loss as in Snell's Law, or Schlieren index changes as in transverse index changes. An index change gives rise to a change in the optical power transmitted through the flow cell and thus a change in the measured absorbence.

When qualifying a flow cell or light pipe for chemical analysis, the American Standards on Testing and Materials methods Designation E 1657-94 define the method for determining the apparent change in the absorbence at the isobestic point, where the absorbence's are equal, for two solvents, methanol and cyclohexane. This refractive index (RI) sensitivity measurement appears as an apparent absorption due to effects from index of refraction differences between the two solvents. Due to refraction (e.g. Snell's Law), the efficiency of coupling light into or out of the light pipe may change producing a baseline absorbence change. Cladding modes could also be induced, changing the transmission and apparent absorbence. Furthermore, since the light interacts with the Teflon AF walls, the light pipe performance becomes sensitive to the surface quality and to any factors that alter or change the Teflon AF. Other relevant physical parameters include temperature, pressure, and gas permeability.

OBJECTS AND SUMMARY OF THE INVENTION

It is a general object of the present invention to provide a fiber-coupled liquid sample analyzer having high detection sensitivity, high resolution, high dynamic range, low RI sensitivity, low thermo-mechanical induced noise, achieve high pressure operation, and be easy to manufacture in a cost effective manner.

It is another object of the present invention to provide a liquid sample analyzer including a liquid flow cell which provide high transmissivity with low scattering.

It is a further object of the present invention to provide a liquid sample analyzer which has low sensitivity to temperature and pressure changes.

It is another object of the present invention to provide a sample analyzer having a liquid flow cell which is located adjacent the liquid sample source and remote from the light source and the signal processing system.

The foregoing and other objects of the invention are achieved by a liquid sample analyzer which includes fiber-coupled light sources which are connected with a fiber-optic beam combiner to apply light to a fiber optic cable or fiber coupled to a flow cell or liquid waveguide that can be remotely located near a separation column. Another fiber optic cable couples light from the flow cell or light pipe to a spectrum analyzer. The flow cell is in the form of a liquid waveguide or light pipe of tubular construction, having first and second ends through which the sample liquid flows. First and second end caps are sealed to said first and second ends of said light pipe. An input liquid passage is formed in said first end cap spaced from the first end of the light pipe. The fiber optic cable extends into and is sealed to said first end cap with its end optically coupled to said one end of said light pipe so that all fiber optic light modes are captured by said light pipe to propagate therealong. An annular space surrounds the end of said optic cable fiber and extends between said input passage and the one end of said light pipe whereby input liquid flows around and along said end of said optic cable into said light pipe to provide a smooth laminar flow of sample liquid past the end of said optic cable. An output passage is formed in said second end cap spaced from the second end of the liquid light pipe. An output optical cable extends into and is sealed to said second end cap with its end optically coupled to said second end of said light pipe so that all optical modes which propagate along said light pipe are captured by the output optic cable and applied to a processing system. An annular space surrounds the end of said output optic cable between said output passage and the second end of said light pipe whereby liquid flowing from said light pipe flows around and along the end of said output optic cable to provide a smooth laminar output flow of sample past the end of said output cable.

BRIEF DESCRIPTION OF THE DRAWINGS

The invention will be more clearly understood from the following description when read in conjunction with the accompanying drawings in which.

DETAILED DESCRIPTION OF THE INVENTION

Figure 1:
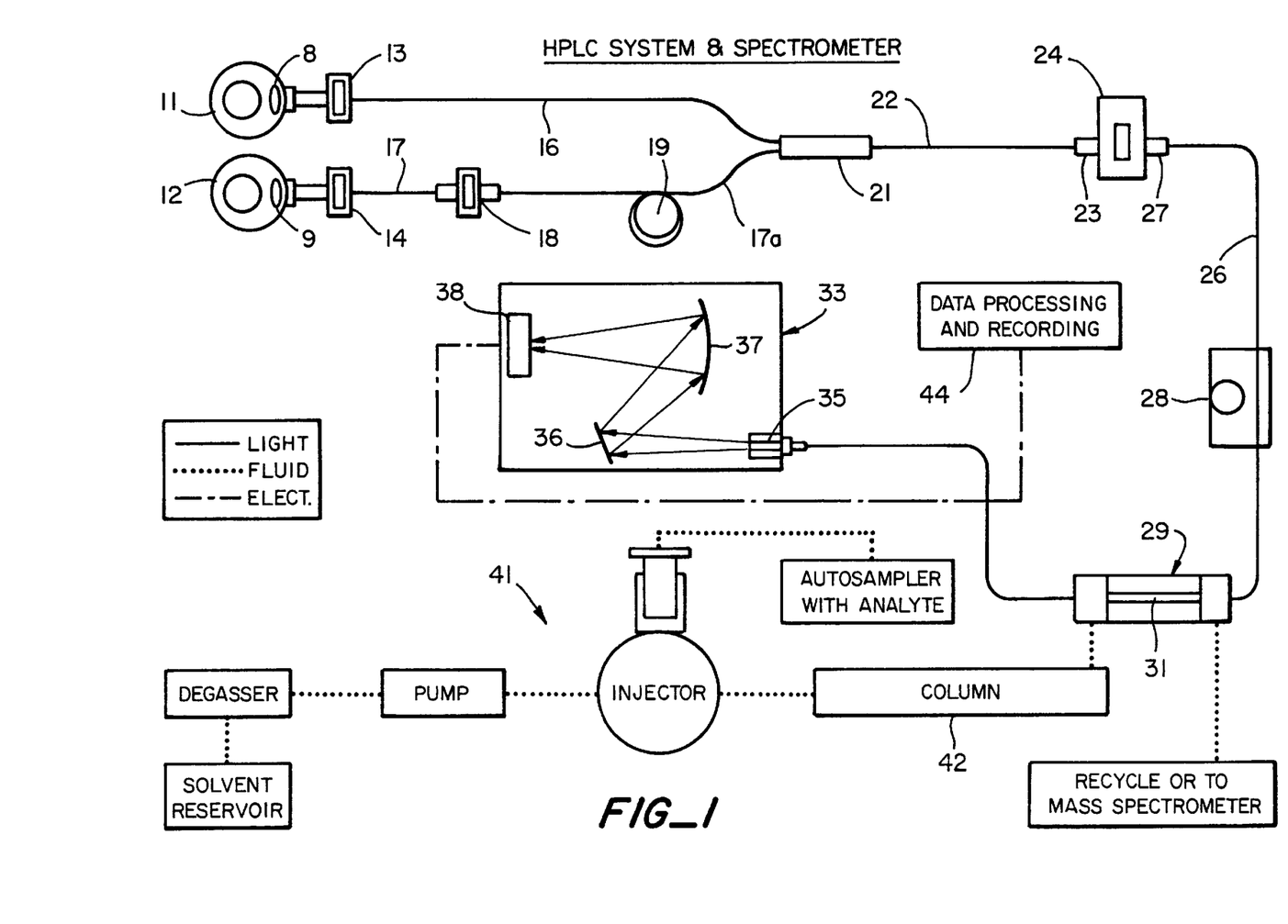
FIG. 1 is a schematic diagram of a liquid analyzing system in accordance with one embodiment of the present invention.

A fiber-coupled liquid sample analyzer system with a flow-through liquid waveguide or light pipe which can be located adjacent the analyte source is illustrated in FIG. 1. The analyzer includes a dual-lamp light source including, for example, a deuterium source 11 and a tungsten source 12, providing a high-intensity light level across the 190 nm to 800 nm spectral range. The light from the light sources 11 and 12 is focused by lenses 8 and 9, attenuated by attenuators 13 and 14, and coupled to optical fibers or cables 16 and 17. Light from the tungsten source is filtered by filter 18, applied to a mode adjuster 19, coupled to a coupler 21, via the optical fiber 17a. The mode coupler combines the light from the two sources. The combined light travels along the optical fiber 22 to a collimating 23 lens which provides an input to filter and calibration means 24 and in turn is coupled to the optical cable or fiber 26 by a lens 27. A mode scrambler or mode stripper 28 receives the light and provides an input to a flow-through cell 29 and light pipe 31 constructed in accordance with one embodiment of the present invention, to be presently described in detail. The output light from the flow-through cell 29 is coupled to a spectrometer 33 by an optical cable 34 with the fibers arranged in the form of a fan at the entrance aperture 35 to provide a fan beam of light simulating the entrance slit of a typical spectrometer. The spectrometer includes a mirror 36, grating 37 and detector assembly 38. The action of the spectrometer is to break the light into its component frequency bands and provide an output signal representing amplitude of the light as a function of wavelength.

Schematically illustrated in FIG. 1 is a high-pressure liquid chromatograph system 41 in which an analyte is supplied to a separation column 42, where the analyte components are separated. The output liquid is applied as the input to the flow-through cell 29, and the output liquid from the flow-through cell can be recycled, applied to a mass spectrometer or directed to waste disposal. The liquid leaving the column and flowing through the flow cell light pipe 31 attenuates the light in proportion to the absorbence constituents of the sample. The output light is applied to the spectrometer which provides an output signal which is proportional to the light intensity at each wavelength. The output signal is applied to a data processing and recording system 44 which may for example compare the signal to a reference signal and provide an indication of the absorbence at each of the wavelengths. It is observed that by use of the fiber optic cables, the flow-through cell 29 can be located closely adjacent to the high-pressure liquid chromatography column 42 whereby separated samples do not have an opportunity to disperse as they are transported to the flow cell.

Figure 2:
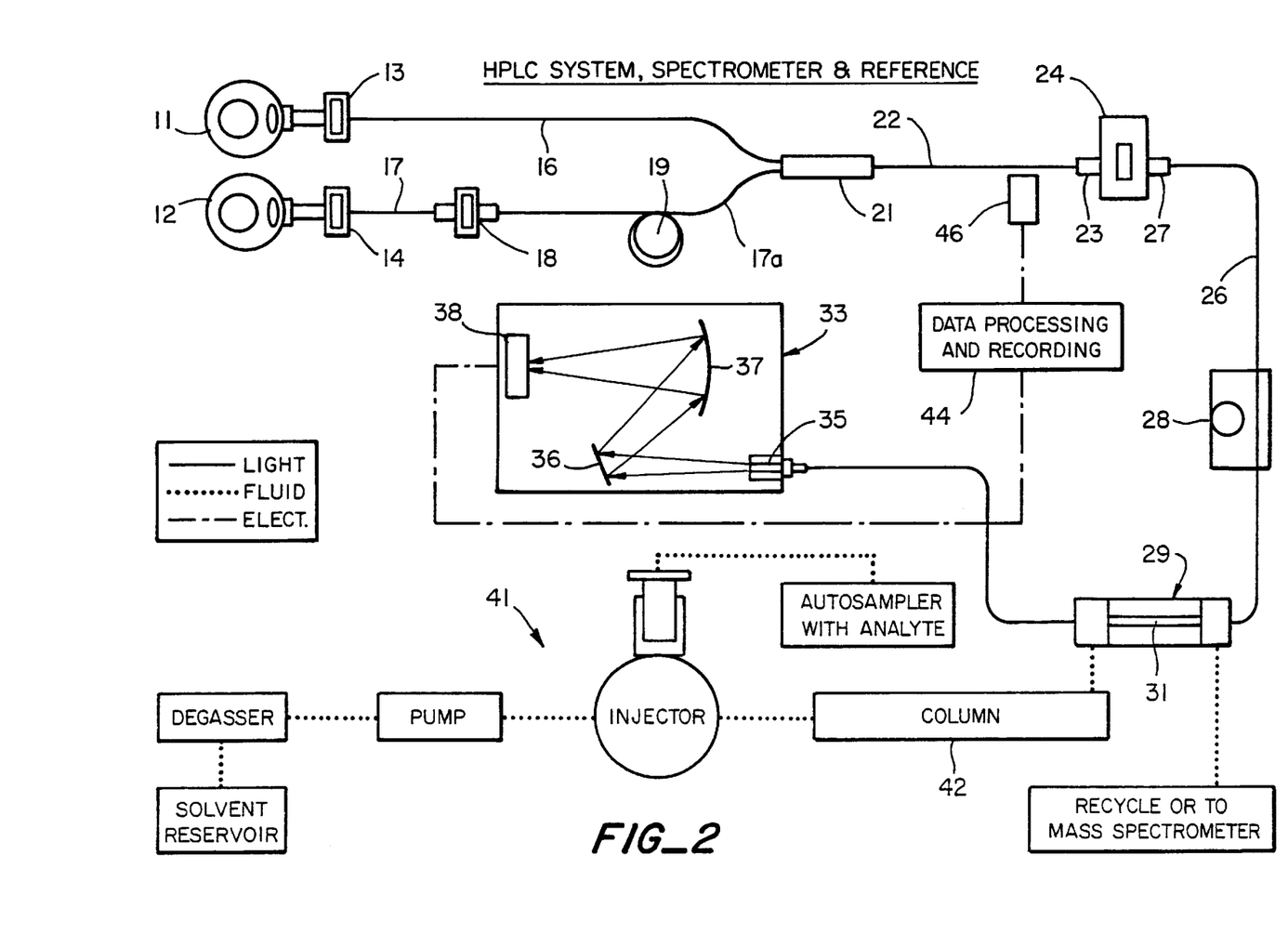
FIG. 2 is a schematic diagram of the liquid analyzing system that employs a reference detector.

FIG. 2 shows a system substantially identical to that of FIG. 1, and includes like reference numerals for like parts. In this system, a reference signal corresponding to the input light intensity is obtained by a detector 46 which receives output from the coupler 21 and applies the signal to the data processing and recording system 44, whereby the signal is used to correct for any fluctuations in light intensity.

Figure 3:
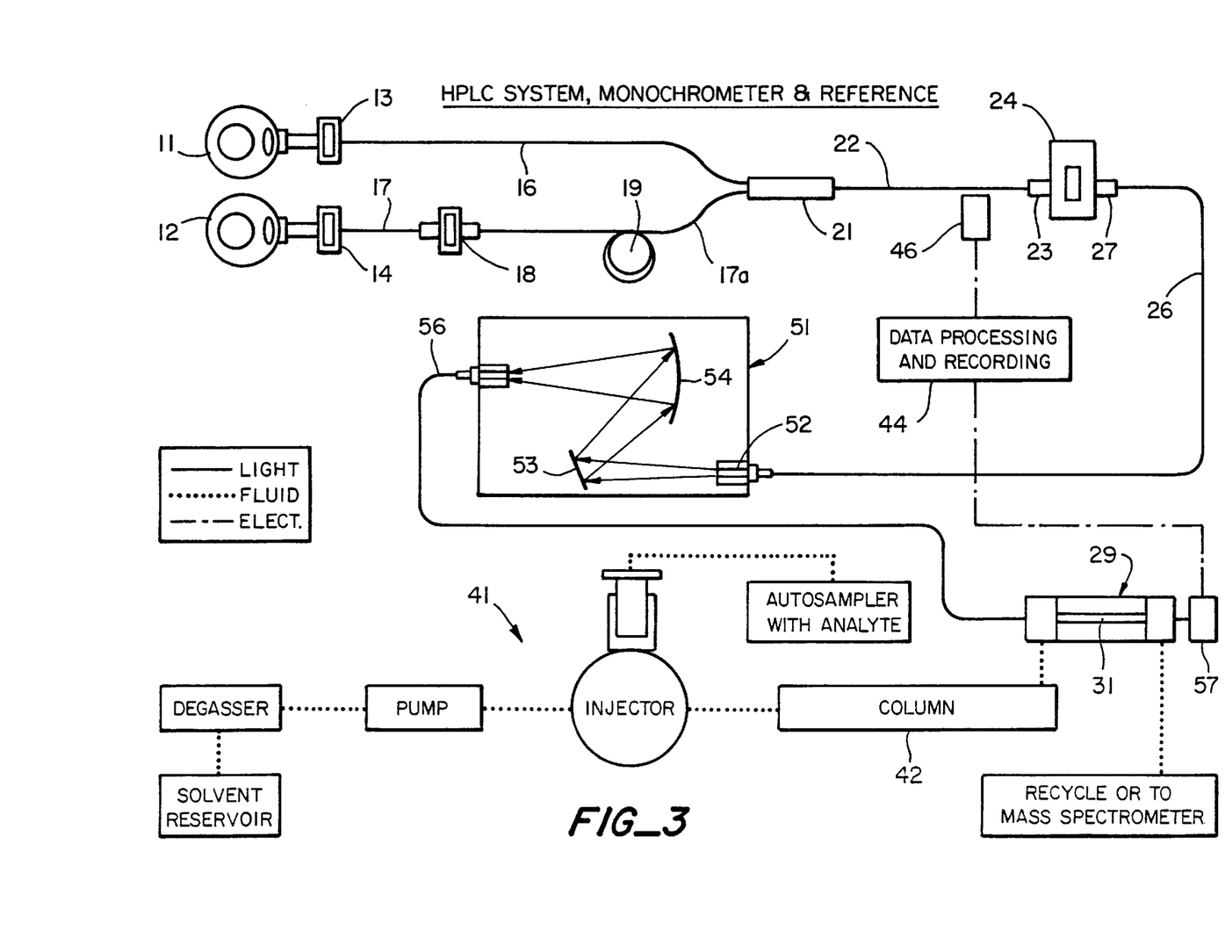
FIG. 3 is a schematic diagram of the liquid analyzing system that employs a monochrometer.

FIG. 3 illustrates another analyzing system which can be used with the flow-through cell of the present invention, which cell can be remotely located. In this system, the light traveling along the optical cable or fiber 26 is applied to a monochrometer 51 which includes a fiber beam shaper 52, mirror 53 and scanning grating 54. The action of the monochrometer is to sequentially apply light of different wavelengths to the optical cable or fiber 56, which is connected at the input to the flow-through liquid cell 29. In other words, light at various wavelengths is scanned to pass through the flow-through cell. The output is detected by detector 57 whose output is applied to a data processing recording system which, as in the embodiment of FIG. 2, receives a reference signal and processes the signal to provide an indication of absorbence for each wavelength of light directed through the flow-through cell 29.

Figure 4:
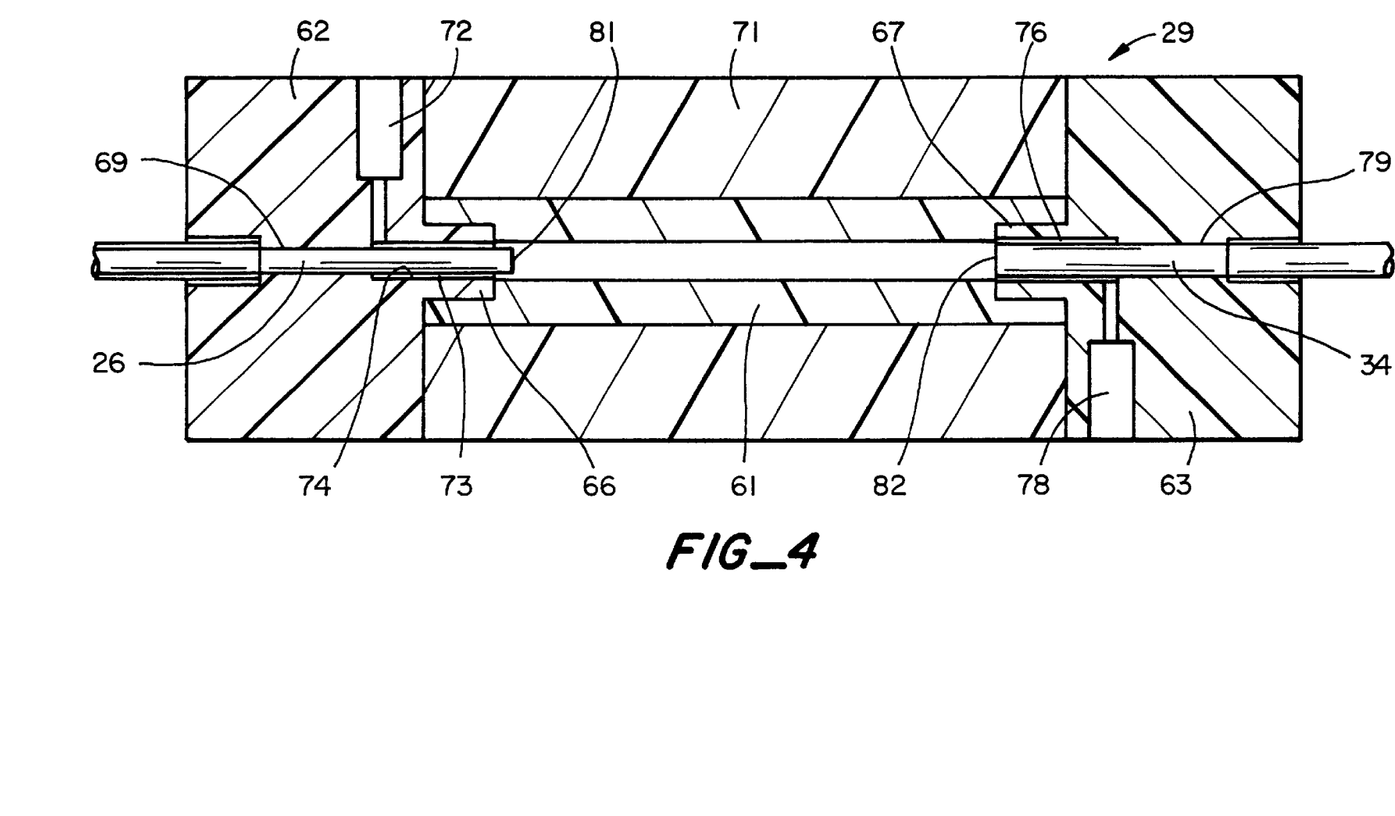
FIG. 4 is an enlarged sectional view of a flow-through liquid cell for use in the liquid analyzing systems shown in FIGS. 1–3.

The liquid sample flow-through cell 29 is shown in detail in FIG. 4. The cell includes a light pipe 61 through which the liquid flows. Light is transmitted along the light pipe. The light pipe and flowing liquid form a waveguide which guides the light therealong. The light pipe 61 is of tubular construction and made of a material whose index of refraction is smaller than that of the liquid sample which flows therethrough. End caps 62 and 63 are sealed to the ends of the light pipe. The end caps 62 and 63 can be made of polyetheretherketone (PEEK) and include end pieces 66 and 67 which extend into and seal the ends of the light pipe to the endcaps. The input optical fiber or cable 26, which may be coated with Teflon AF to transmit the maximum number of modes, is compression fit into the bore 69 in end cap 62. The light pipe has an inner diameter that is equal to or larger than the diameter of the input fiber or cable whereby all light output modes of the fiber are captured by the light pipe. The light pipe 61 is enclosed in a body 71 of a material having a low gas permeability, and is sealed to the end caps 62 and 63. The body 71 also prevents expansion of the light pipe when liquids at high pressure flow through the flow cell. In the embodiment shown in FIG. 4, the input optical cable extends into the core of the light pipe 61. It will be understood, as will be explained herein, that the end of the optical fiber need only be coupled to the light pipe so that the light pipe captures all modes transmitted by the optical fiber. A liquid sample input passage 72 is formed in the end cap 62 and terminates at the annular space 73 formed by the gap between the end of the fiber and the enlarged bore 74 of the end cap. This provides that the liquid flows smoothly along and past the end of the fiber, that is that there is substantially laminar flow of liquid into the light pipe. The liquid leaving the light pipe flows through the annular space 76 between the output fiber 34 and the end cap 63, and through the passage 78. The output fiber 34 is also compression fit into the bore 79 formed in the end cap 63. The output fiber has a diameter which is equal to or larger than that of the light pipe so that it captures all of the light output modes so as to maximize transmission.

Mode controller 28, FIGS. 1 and 2, strips away optical modes which would be unguided in the light pipe that cause refractive index sensitivity (RI) problems, baseline noise, and to optimize the modes injected into the light pipe to obtain high sensitivity. A suitable mode controller can be obtained from Newport Research Corporation, Irvine, Calif. and adapted to multimode fiber. The light is emitted from the end 81 of the fiber 26 into the liquid in the light pipe core. In the example illustrated in FIG. 4, the end of the light pipe extends into the core of the light pipe whereby all light modes are captured and flow along the light pipe. The light transmitted through the liquid waveguide, formed by the light pipe and flowing liquid, is collected by the end 82 of the output optical fiber 34 and transmitted along the fiber to the spectrophotometer or polychrometer 33 which provides the output signal representing light intensity as a function of wavelength.

The following detailed description and analysis is directed to characteristics of the light pipe or liquid waveguide which enable the analyzer to operate with improved sensitivity. Higher order modes which are coupled into the liquid waveguide can become noise sources, i.e., they will not travel in the analyte but rather through the light pipe (cladding) and into the detection system as background noise. This is especially true for relatively short multimode liquid waveguides since it takes many meters to kilometers for the unguided modes to be stripped away. Given the length of light pipes used in chromatography, the unguided modes will not be stripped away by the light pipe.

When a waveguide is curved, macro-bending losses occur. That is, a straight liquid waveguide supports more modes than a bent liquid waveguide. So, in principle a straight liquid waveguide is preferable to a curved guide. To effectively utilize a curved liquid waveguide for LC, modes must be launched that are supported by the configuration of the guide (straight or curved), are efficiently coupled by the optical fiber-to-light pipe interface connection, and are supported by the surface quality of the guide. Launching and preserving the correct guided modes is also important when the RI sensitivity is considered.

The mode stripper may be used to remove the cladding modes. The waveguide index relationship is, $$n_{core} > n_{Teflon\ AF} > n_{air}.$$

Typical core solvents in liquid chromatography (LC) are water ($n_{core}$=1.333), methanol ($n_{core}$=1.328) or acetonitrile ($n_{core}$=1.344). Thus, Teflon AF 2400 (n=1.294) or Teflon AF 1600 (1.31) can be used for the light pipe. The lower the index of refraction of the light pipe, the larger the acceptance angles of the light pipe. This will permit more light to be focused into the light pipe (a greater acceptance angle) increasing the absorbence measurement dynamic range and absorbence sensitivity of the light pipe.

The range of modes that can propagate in a liquid waveguide depends on the light pipe design and the angle over which light is launched into the light pipe. The light pipe design and light launching conditions should provide for the launching and guiding of higher order modes, since the higher order modes travel a longer distance in the liquid thereby increasing the absorbence sensitivity. If there is sufficient power in the higher order modes, blocking the lower order modes before injection into the light pipe will increase the absorbence sensitivity of the light pipe. The acceptance half-angle (or cut-off angle) of a liquid waveguide is determined by the expression $$\theta_{accept.} = \arcsin[(1/n_{ext})\sqrt{(n_1^2 - n_2^2)}].$$

Here, $n_1$ and $n_2$ are the index of refraction of the core (solvent) and light pipe (Teflon AF) respectively and $n_{ext}$ is the external medium or interface material. Usually the acceptance angle of a liquid waveguide is given without $n_{ext}$, i.e., $n_{ext}$=1 for an air interface. However, with a liquid waveguide the solvent must be contained within the guide by a window of some type. Using the previous expression, the acceptance angles for three different interfaces is given in Table 1.

TABLE 1

| Solvent | Solvent Index | Teflon AF Index | Interface Index | Acceptance Angle (deg) | Full Angle (deg) |
|---|---|---|---|---|---|
| MeOH | 1.328 | 1.294 | 1.000 | 17.37 | 34.74 |
| Water | 1.333 | 1.294 | 1.000 | 18.67 | 37.34 |
| Cyclo | 1.426 | 1.294 | 1.000 | 36.81 | 73.63 |
| Solvent | Solvent Index | Teflon AF Index | Interface Index | Acceptance Angle (deg) | Full Angle (deg) |
| MeOH | 1.328 | 1.294 | 1.294 | 13.34 | 26.68 |
| Water | 1.333 | 1.294 | 1.294 | 14.32 | 28.64 |
| Cyclo | 1.426 | 1.294 | 1.294 | 27.58 | 55.17 |
| Solvent | Solvent Index | Teflon AF Index | Interface Index | Acceptance Angle (deg) | Full Angle (deg) |
| MeOH | 1.328 | 1.294 | 1.460 | 11.80 | 23.60 |
| Water | 1.333 | 1.294 | 1.460 | 12.66 | 25.33 |
| Cyclo | 1.426 | 1.294 | 1.460 | 24.23 | 48.46 |

It can be observed that (1) more light modes propagate with cyclohexane, and (2) the lower the index of refraction of the interface material, the greater the number of modes. The former is dictated by the chromatography and the latter can be controlled by the design of the light pipe. Light can be coupled into the light pipe with either a lens or optical fiber that produces the optimum cone angle of light.

The present invention advocates the use of an optical fiber whose tip is coated with Teflon AF with the fiber tip in intimate contact with the solvent. For this configuration, the light launch conditions into the optical fiber, propagation angle of the light within the optical fiber, through the Teflon AF, and into the light pipe is found from the acceptance angle and Snell's law $$n_{air} \sin \theta_{air} = n_{fiber} \sin \theta_{fiber} = n_{AF} \sin \theta_{acceptance}$$

where $n_{air}$ is the index of air, $n_{fiber}$ is the fiber core index of refraction, and $n_{AF}$ is the index of the Teflon AF light pipe. Light launch and propagation conditions are given in Table 2 for an optical fiber with and without Teflon AF on the tip that is in direct contact with methanol in the liquid waveguide.

TABLE 2

Light launch $\theta_{air}$ and propagation angles for different interface materials.

| Angle (deg) | Teflon AF Interface | Glass Interface |
|---|---|---|
| $\theta_{MeOH}$ | 13.0 | 11.5 |
| $\theta_{accept.}$ | 13.3 | 11.8 |
| $\theta_{fiber}$ | 11.8 | 10.4 |
| $\theta_{air}$ | 17.4 | 15.3 |

Although the increase in the acceptance angle from glass to Teflon AF appears small, it increases the power density (which is a quadratic function with radius) that can be input into the light pipe and increases the number of higher order modes. This becomes more important when small spot sizes are needed for coupling into small diameter fibers used for a LC light pipe. In this case, a faster lens is needed to create a small spot size. In addition, the Teflon AF coating on the fiber will act as an antireflection (AR) coating, further increasing the transmitted power into the light pipe.

Obviously, light should be launched into the optical fiber by the lenses 8 and 9 at the proper acceptance cone angle. Mode mixing within the liquid waveguide should be minimized to avoid out-coupling of light (loss) into the light pipe.) Mode mixing in a high NA (numerical aperture) or high acceptance angle fiber would shift the light into the allowed higher order modes of the fiber. It is possible that these higher order modes would not be guided in the light pipe when filled with methanol but would be guided when filled with cyclohexane. This leads to refractive index or RI sensitivity and promotes a baseline drift during reverse phase chromatography. If necessary, a mode stripper can be used to eliminate some higher order modes before directing the light into the liquid waveguide. In HPLC light with wavelengths from 190 nm to 800 nm is used. The ultraviolet light (190 nm to 400 nm) usually photo-darkens the optical fiber making it too absorbing for use, called solarization. Non-solarizing optical fibers are available from Polymicro Technologies in Phoenix, Ariz. They are made with a core of high purity silica (sometimes defect compensated) and with a cladding of either heavy metal doped silica or Teflon AF. There are three fibers currently available, with NA's of 0.22, 0.33, and 0.66 relative to an air interface with acceptance angles shown in Table 3. Using a 0.33 NA fiber will allow one to launch more guided modes into the light pipe with methanol as the liquid core.

TABLE 3

Table of optical fiber specifications.

| Core | Cladding | Interface index | Accept. Angle (deg) | Internal Angle (deg) | NA |
|---|---|---|---|---|---|
| 1.46 | 1.300 | 1.00 | 41.6 | 27.1 | 0.66 |
| 1.46 | 1.443 | 1.00 | 12.8 | 8.8 | 0.22 |
| 1.46 | 1.423 | 1.00 | 19.1 | 12.9 | 0.33 |

The refractive index sensitivity (RI) is determined by the transmission T of the light pipe at 280 nm for a core of HPLC grade methanol and then for a core of cyclohexane. The difference in their absorbance (A=log[1/T]) gives the RI:

$$RI = A_{MeOH} - A_{cyclo} = \log[1/T_{MeOH}] - \log[1/T_{cycl}].$$

The absorbance, Fresnel reflection, refraction, the Schlerien effect, and other factors determine the transmission for each solvent. The absorbance of methanol and cyclohexane are very nearly equivalent at 280 nm and so only the index dependent factors play a role in determining the detector signal. Acceptable RI sensitivity values are usually less than 10 mAU of equivalent baseline deviation, the smaller the better. A 2% difference in transmission between MeOH and cyclohexane waveguides will produce 8.7 mAU's of RI.

RI sensitivity depends on the modes launched into the light pipe since the critical angle is index dependent. Snell's law cannot be satisfied at the liquid core—Teflon AF cladding interface when the angle of the light with respect to the normal $\theta_1$ is greater than the critical angle $\theta_C$, i.e., $\theta_1 > \theta_C$ or $\theta_1 - \theta_C > 0$. $\theta_1$ is determined from Snell's law where $$\theta_1 = 90 - \theta_r = \arccos(n_i/n_1 \sin \theta_i).$$

The angle of incidence external to the liquid waveguide is $\theta_i$ with an index of refraction of $n_i$. The critical angle is $$\theta_{Critical} = \arcsin(n_2/n_1).$$

Figure 5:
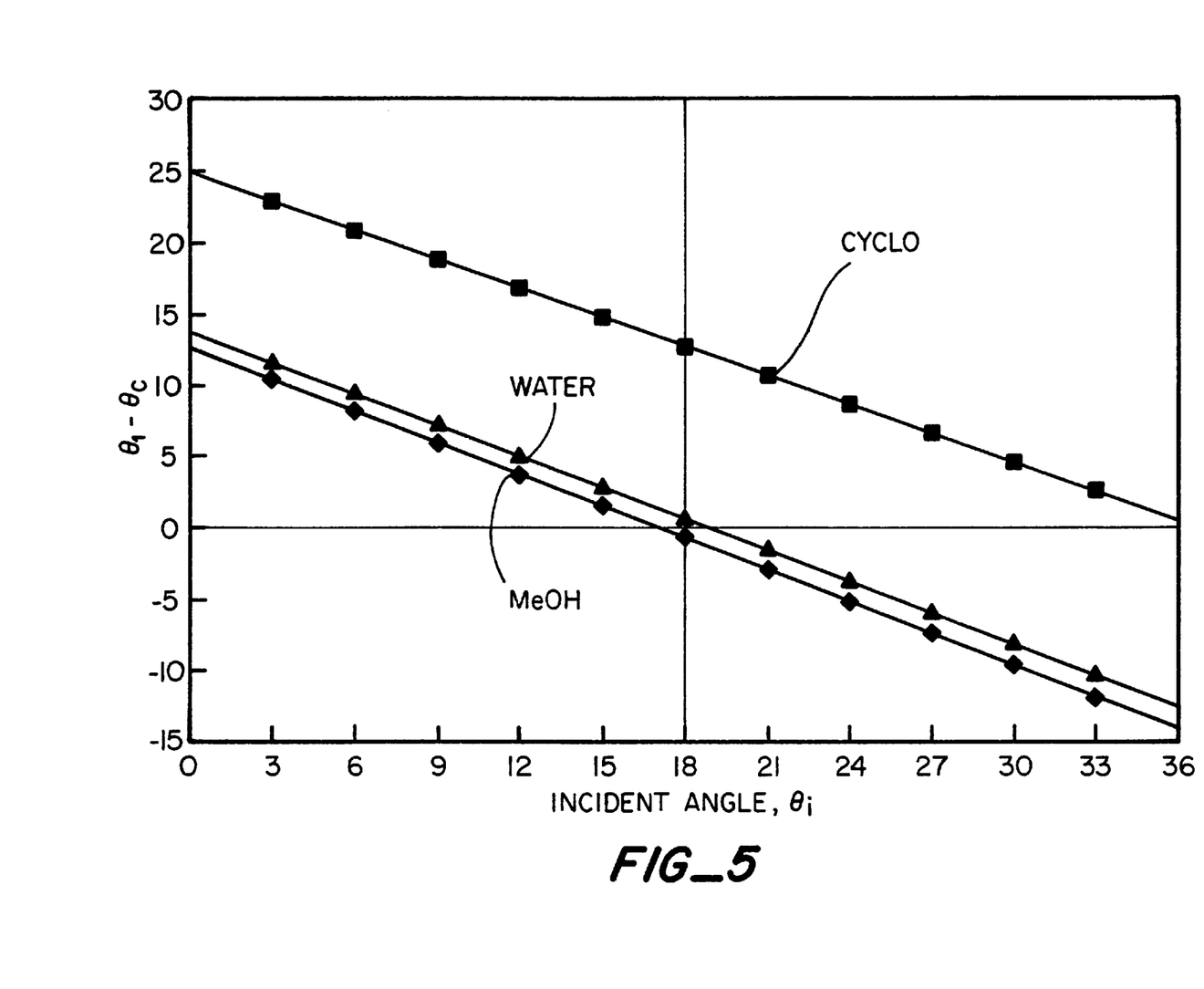
FIG. 5 is a plot of $\theta_1 - \theta_C$ versus $\theta_i$ for three different liquid cores.

FIG. 5 is a plot of $\theta_1 - \theta_C$ versus $\theta_i$ for three different liquid cores with $n_i = 1$. When $\theta_1 - \theta_C > 0$ all the light is totally internally reflected and guided. When $\theta_1 - \theta_C < 0$ the light is refracted and reflected at the interface, the transmission loss increases for those rays. This occurs for MeOH and H$_2$O at a smaller incidence or acceptance angle than cyclohexane and beyond which increases the RI.

Another way to understand the differences in coupling losses for two different liquid waveguides can be observed through their mismatch in numerical apertures with respect to the optical fiber. Each solvent creates a liquid waveguide with a unique $NA = \sqrt{(n_1^2 - n_2^2)}$. The transmission for NA mismatched coupled waveguides (fiber to liquid waveguide) is $T = [NA_1/NA_2]^2$. The absorbance for a NA mismatch may then be expressed as $$A = \log[(NA_{solvent}/NA_{fiber})^2]$$

The loss or apparent absorbance is zero if the transmitting fiber NA is smaller than the solvent NA. It is preferable to have the receiving waveguide with the larger NA to maximize the transmission. Further, each solvent produces a different NA for the liquid waveguide and this can lead to RI sensitivity. The NA's of a methanol or cyclohexane—Teflon AF (2400) liquid waveguide are 0.3 and 0.6 respectively. Table 4 gives the effective absorbance and the resulting RI sensitivity for these conditions.

TABLE 4

Effective absorbances (A) and RI sensitivity due to a numerical aperture (NA) mismatch.

| $NA_{MeOH}$ | $NA_{cyclo}$ | $NA_{fiber}$ | $A_{meoh}$ | $A_{cyclo}$ | RI(AU) |
|---|---|---|---|---|---|
| 0.30 | 0.60 | 0.33 | −0.09 | 0.52 | −0.61 |

These observations lead to the following design considerations for minimizing the RI sensitivity and maximizing the light coupling, $$NA_{InOF} \leq NA_{LW} \leq NA_{OutOF}.$$

Here $NA_{InOF}$, $NA_{LW}$, and $NA_{OutOF}$ are the numerical aperture of the input optical fiber, liquid waveguide, and output optical fiber respectively. In addition, for maximum coupling, the input optical fiber diameter $d_{InOF}$ should be equivalent to or less than the liquid waveguide bore $d_{LW}$, and the ouput optical fiber diameter $d_{OutOF}$ should be equivalent to or greater than the liquid waveguide bore, $$d_{InOF} \leq d_{LW} \leq d_{OutOF}.$$

Another factor that determines the RI is the proximity of the optical fiber to the bore of the Teflon AF light pipe. In previous designs, a gap exists to allow solvent to flow in and out of the light pipe. The absorbance for a gap of distance z with index $n_0$ between two fibers with numerical apertures NA and radii of r is $$A = \log[1/(1 - zNA/2rn_0)]$$

Since the gap can be filled with either MeOH, $n_0 = 1.328$, or cyclohexane, $n_0 32\ 1.426$, there can be difference in the optical losses when a gap exists leading to RI effects. To have acceptable RI values, it would be preferable to keep the optical fiber within 0.010 inch (~6 mAU of RI) of the light pipe bore when the diameters of the light pipe and optical fiber and their numerical apertures are matched.

Another, source of RI is angular misalignment where the absorbance is express as $$A = \log[1/(1 - (8n_0 \sin \theta)/(3\pi NA))],$$

where $\theta$ is the angle of the fiber axis with respect to the optical axis of the light pipe. The angular miss-alignment should be kept below 1 degree to obtain RI sensitivity below 7 mAU. If the optical fiber is inserted into the light pipe there must be clearance for fluid to pass. The clearance makes possible some angular misalignment so that putting the light input fiber into the light pipe does not necessarily eliminate the light loss from angular misalignment or the RI sensitivity to angular misalignment.

Bending changes the angle of incidence of the light onto the core-cladding interface and changes the conditions for Total Internal Reflection, increasing the out-coupling or loss. Bending losses will also change for a liquid waveguide depending on the liquid within the guide and give rise to RI sensitivity. In addition, coiling the liquid waveguide will induce higher order mode out-coupling reducing the detection sensitivity. Further, light could propagate in the cladding and possibly be captured by the output fiber as noise. Cladding modes should be avoided since they will be a baseline noise source that will reduce the detection sensitivity and dynamic range. If the liquid waveguide is coiled the input modes must be reduced, via a mode controller, to those that are not lossy for that degree of bending and resultant mode mixing.

The aforementioned index dependent absorbance differences, including 1) Fresnel reflection, 2) NA mismatch, 3) Longitudinal separation, 4) Angular misalignment, and 5) Bending losses induce RI's that are cumulative. The RI sensitivity (and thus baseline disturbance) will be unacceptably high unless the light pipe is designed to avoid these index dependent losses.

Figure 6:
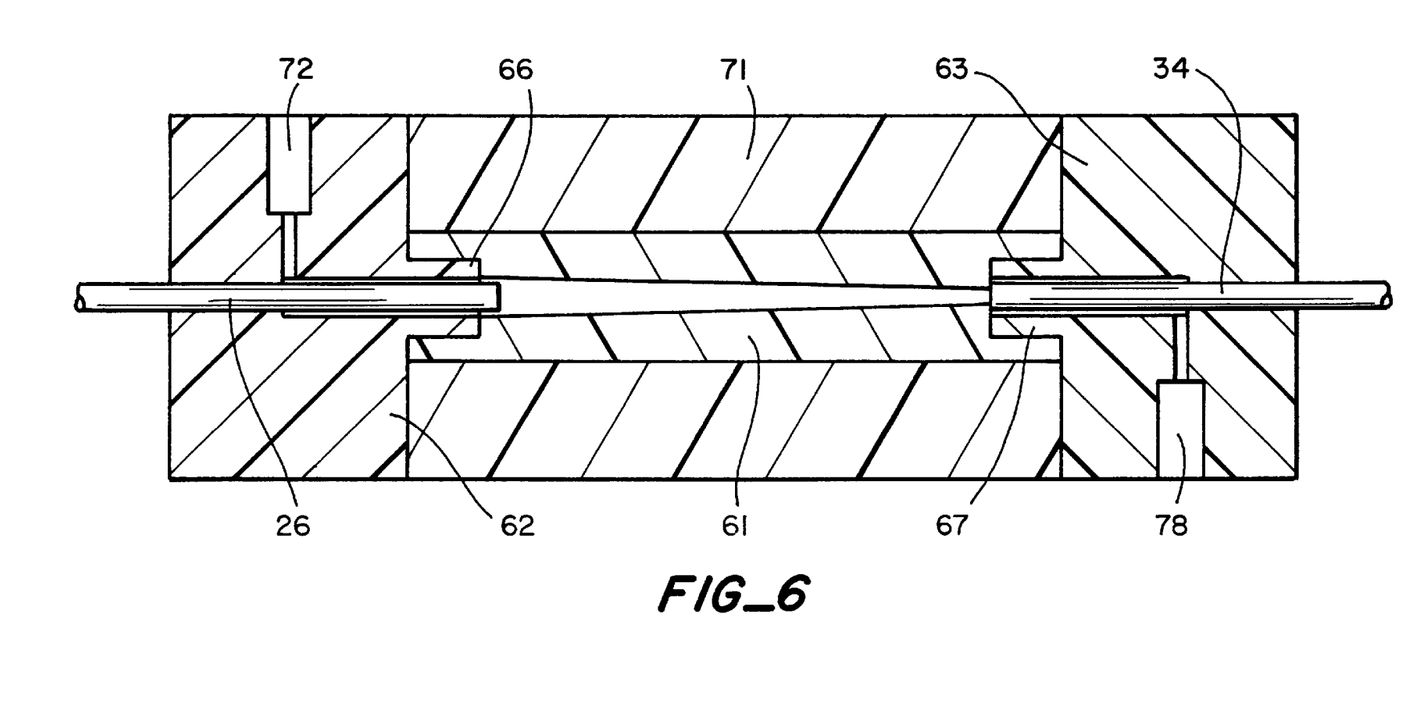
FIG. 6 is an enlarged sectional view of a flow-through liquid cell having a tapered light pipe for use in analyzing systems of the type shown in FIGS. 1–3.

Using the equation for the acceptance half-angle of the optical fiber permits half-angles of 12.9 degrees or less. However, higher angles are supported in a multimode optical fiber, but may not be supported by the liquid waveguide. In addition, for the physical conditions modeled, there is a tolerance in the RI for diameters between 0.020 inch and 0.022 inch. Further, biasing to larger diameters (>0.02 inch) is better than smaller diameters (<0.02). This tolerance also shows that it is possible, and potentially desirable, to taper the light pipe. By way of example, referring to FIG. 6, where like parts are provided with the same reference numbers as FIG. 4, the input diameter of the light pipe 61 would be 0.022 inch, and the output diameter 0.020 inch. In this way, input and output optical fibers 26 and 34 of equivalent diameter could be used.

It is important to maintain laminar flow throughout the light pipe to avoid turbulence that causes band broadening and light scattering. It is also important that the fluid input does not disturb the light input. In previous light pipes and flow cells the fluid entered parallel to the input window or normal to the optical path and then made a sharp turn into the liquid waveguide.

In the case of a fiber coupled light pipe, an orifice along the wall of the light pipe is detrimental to the total internal reflection process that sustains the passage of light through the liquid waveguide. Further, the input tubing diameters are typically 0.010 for milli-liter volume light pipes and a 0.010 hole into a 0.020 diameter light pipe requires removal of a significant fraction of the wall.

A better approach is that shown in FIG. 4. In the first design, a seal between the end cap and the Teflon AF light pipe is created by the radial compression of the Teflon AF over the PEEK tip. The fluid enters the liquid waveguide by first flowing around the optical fiber. The fluid enters a manifold or annular space so that it completely surrounds the optical fiber before entering symmetrically into the liquid waveguide. This design, or others envisioned by what is taught here, accomplish sealing, and fluid and light introduction without breaking the continuity of the liquid waveguide and total internal reflection process.

The pump of a HPLC system mostly operates in a constant flow mode so the output pressure will change as the viscosity of the solvent changes. During gradient elution the viscosity also changes. The pressure change is directly proportional to the viscosity change. Since Teflon AF can expand from pressure changes, the core diameter of the light pipe can change. These changes are minimized by the body 71. On the light input end of the light pipe, pressure induced expansion can increase the light acceptance aperture, but on the light output end expansion can increase the light loss. If the light input end of the Teflon AF initially captures all the modes injected by the optical fiber, then expansion will have little effect but contraction due to a pressure decrease could affect the coupling. Where the light is coupled from the Teflon AF light pipe to the output optical fiber, a pressure increase could cause the guide to expand larger than the optical fiber. The increase in diameter of the guide, which could occur during a reverse phase gradient, would cause a diameter mismatch between the bore of the Teflon AF and the out-coupling optical fiber.

Minor contraction of the Teflon AF light pipe on the light output end would produce little change in the light coupled from the light pipe into the fiber. Many combinations of these conditions are possible depending on the design of the light pipe and range of pressure changes and can produce RI sensitivity and pressure dependent short-term noise. Using the previous inequalities on numerical apertures and diameters, adjusted to take into account the pressure changes, will avoid the pressure sensitivity of the light pipe. In addition, controlling the modes will also control the sensitivity of the light pipe to pressure.

Controlling the modes is essential to optimizing the performance of a liquid waveguide used from chromatography applications. All of the RI issues can be addressed and controlled with a mode controller. That is, controlling the light input cone angle injected into the optical fiber can select the modes that propagate through the system. This is accomplished with an adjustable lens system by an adjustable iris, spatial blocking filters, a diffractive element or a combination of these elements. In addition, after the light has been injected into the optical fiber, a fiber mode stripper can be used to eliminate unwanted higher order modes.

For some light sources the light power is not equivalently distributed throughout the mode spectrum. Mode mixing or scrambling can be done within an optical fiber that is tightly coiled to produce a spatially uniform light source.

Mode mixing is important when the light source is non-homogeneous. This is usually the case for tungsten-halogen lamps used in LC. Producing a homogeneous beam helps avoid photo bleaching from hot-spots of high intensity. Mode mixing is typically accomplished by coiling the fiber as shown at 19, FIGS. 1–3, or by applying sharp bends along a short section of the fiber.

Diffusely scattering light will add to the noise of the system if is not absorbed by the analyte and subsequently enters the detection system. Optical loss will arise from scattering that occurs if the liquid-Teflon AF interface is not "optically smooth". As discussed by Altkom et al., the inner surface quality can also produce loss differences depending on the solvent. These differences will give rise to a RI effect. For instance, if the transmission difference due to scattering losses between two solvents is 1.1% this will lead to a RI sensitivity equivalent to −5 mAU. Scattering is proportional to the roughness divided by the wavelength squared. Shorter wavelengths scatter more strongly. In ram extrusion of Teflon AF, the inner surface quality is established by the extrusion die surface quality and the extrusion process control. Biogeneral, San Diego, Calif., have reported surface variations of less than 0.0003 inch or 7 micrometers. This variation is much greater than the shortest wavelength of light used in LC. Alternatively, pulling Teflon AF from a preform will produce a surface quality that is dependent on the preform quality and the production conditions. Since the scattering losses observed in the literature are unacceptable for UV wavelengths, especially in a long length liquid waveguide, it is necessary to improve the production method and tooling, or post-process Teflon AF, reducing the inner surface roughness. There are methods to control the inner surface quality of the Teflon AF light pipe. To reduce the surface roughness, Teflon AF tube can be extruded onto an ultra-smooth mandrel. After the Teflon AF is cured it can be removed from the mandrel by heating it to thermally expanding the Teflon AF relative to the mandrel. It is also possible to reduce the inner surface roughness after extrusion by using a mandrel. In this process, the Teflon AF is first heated to expand the bore and then an ultra-smooth mandrel is inserted into the bore. The temperature of the Teflon AF is decreased so that it slightly contracts around the mandrel. Sufficient time is given for the Teflon AF to cold flow at the elevated temperature. Pressure may also be applied to assist the flow of Teflon AF so that it conforms to the surface of the mandrel. The mandrel is then removed via the heating process previously described. Other practices in the art to smooth a surface may include polishing with process slurry passing through the bore or plasma etching.

The Teflon AF light pipe thickness should be adjusted to be thicker than the evanescent wave penetration into the light pipe. The electromagnetic field will decay into the light pipe as $$E = E_0 \exp(-\delta/d_p)$$

where $\delta$ is the distance from the interface surface. The penetration depth $d_p$ is a function of the wavelength of light $\lambda$ and the angle of incidence $\theta$ where $$d_p = \lambda/[2 \ast pi \ast (n^2_{core} \ast \sin^2\theta - n^2_{clad})]^{1/2}.$$

The penetration depth increases with wavelength and decreases with increasing angle of incidence. At $\lambda=589$ mn, an angle of incidence of 85°, and for $n_{core}=1.328$ and $n_{clad}=1.294$ the electric field E will fall to 1/e of its initial value at a distance $\delta=d_p=3.4$ micrometers. In general, shorter wavelengths and higher order modes will have lower penetration depths. One can see that the required optical thickness required is very thin. Typically a light pipe cladding thickness is used that is ten times the characteristic penetration depth $d_p$ $$d_{clad} \geq 10 \times d_p$$

Without a buffer or external support, the thickness of the Teflon AF cladding should be increased to accommodate the pressure range of operation. For example, if the maximum internal pressure is 500 psi, and one wishes to have a wall thickness that is three times the burst pressure, then the wall thickness should be approximately 0.028 inch. In addition, pressure changes, due to viscosity changes for a constant flow rate system, can cause the diameter of the light pipe to increase.

The interface to the liquid source must permit the free flow of liquid, preserving laminar flow, and should not disturb the optical power flow through the optical fiber interface. In the present example, FIG. 1, all this is accomplished by an interference fit between the optical fiber and adjoining material. In the case that the compression is too high so as to disturb the optical field, the fiber can be coated with Teflon, which will act as a gasket seal for either compression method. The flexibility of Teflon will minimize the compression of the silica glass fiber and thus avoid disturbing the optical field. The coating can be the buffer or as an additional layer.

Teflon AF has very high gas permeability. In fact, Teflon AF 2400 is now being utilized as a degassing material for HPLC de-gassers. The gas permeability of Teflon AF 2400 is more than two orders of magnitude higher than conventional polymer like polycarbonate. Poly 1-trimethylsilyl-1-propyne, or PTMSP is the only material that exceeds the gas permeability of Teflon AF. Gas in-diffusion can alter the absorbance measurements. Gas in-diffusion effects depend on the flow rate of the solvent, external pressure, and the length of the Teflon AF. High flow rates are generally used in LC and so the light pipe must be very long to require it being placed in a vacuum. Thus, vacuum containment will be appropriate for measuring very low absorbance.

The diameter of the waveguide can be adjusted for applications in $\mu$LC, LC, and CE. Limitations in diameter will only arise from the interconnection between the optical fiber and liquid waveguide. That is, the fiber core diameter must propagate light, of the longest wavelength to be used. For example, in LC the typical wavelength range is from 190 nanometers to 800 micrometers. The minimum core diameter for $\lambda=800$ nm fiber is about 12.5 microns and a light pipe diameter of about 25 microns. Thus, the minimum Teflon AF inside diameter with fiber coupling would be about 10 microns. For a $\mu$LC volume of 10 nL, and a diameter of 10 microns the length would be 12.74 mm, about ten times longer than previous $\mu$LC absorbance measurement cells. Coupling a broad spectrum of light into a small core is difficult even with achromatic lens but can be accomplished with the appropriate reflective surfaces. For LC cells the usual volumes are from 10 to 15 micro-liters. Limitations to the Teflon AF bore when using a fiber input again only depend on the optical fiber. If a window is used instead of a fiber, the Teflon AF bore diameter is controlled by the numerical aperture of the liquid waveguide and the spot size or Teflon AF bore diameter. Using the same bore diameter, 10 microns, and a volume of 10 micro-liters would give a cell length of about 127 meters. Such a cell would find application for ultra-low absorbance detection and shows the scalability of a Teflon AF absorbance liquid waveguide. Typically a 11 micro-liter volume cells has a 0.5 mm diameter and 50 mm lengths giving five times the sensitivity of a standard flow cell.

The volume coefficient of thermal expansion for Teflon AF 2400 is 301 ppm/°C. The thermally induced expansion of Teflon AF does not produce a major effect on the diameter of the light pipe over the operating temperature of an LC instrument. However, temperature induced index changes of the solvent that cause RI problems are know in the art (see U.S. Pat. No. 4,192,614). In an analogous fashion to U.S. Pat. No. 4,192,614, the light pipe outer body should be enclosed in a thermally conductive material, such as steel, or brass, or aluminum, with large thermal mass to help the Teflon AF rapidly reach thermal equilibrium. However, since we wish to have the liquid waveguide unconstrained, the Teflon AF should be brought into thermal contact with the metal enclosure through thermally conductive grease, or silicon glue, or gel, or other appropriate material. Further, as instructed in U.S. Pat. No. 4,192,614, the pipe that conducts the fluid to the flow cell should be made of a thermally conductive material and can be brought into contact with the light pipe outer body so the input fluid is in thermal equilibrium.

Many different harsh chemicals are used in LC and thus the light pipe should be made of inert materials. In addition, protein quantification with LC requires materials that do not denature them, e.g., iron. Teflon AF and PEEK are very inert materials used in the construction of the Light Pipe described herein. In some instances, the optical fiber, made of heavy metal doped fused silica, may attacked by the solvents used in a particular application. However, the optical fiber can be coated with Teflon AF to eliminate this potential problem.

Figure 7:
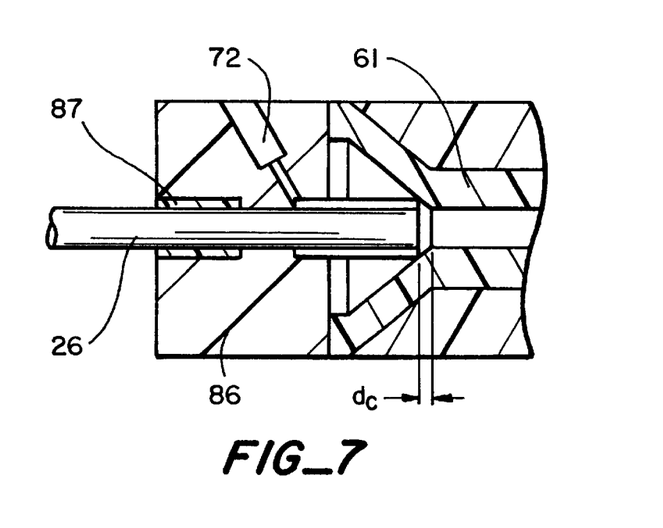
FIG. 7 is a cross-sectional view of the input portion of a flow-through cell having a different arrangement for coupling light into the light pipe.

The input optical fiber need not extend into the bore of the light pipe as shown in FIG. 4. It need only be within a critical distance, which depends on the lowest index of refraction of the solution and the diameters of the optical fiber and light pipe core, and is approximately 0.004 inch or less. FIG. 7 shows a light pipe 61 with its input end spaced from the end of the input fiber 26. The fiber support 86 is sealed to the light pipe 61 by a seal 87. The end of the optical fiber 26 is spaced a distance dc to allow the sample liquid to flow into the light pipe. The distance dc should be no greater than the internal diameter of the light pipe 61 and depends on the solvent index of refraction.

Figure 8:
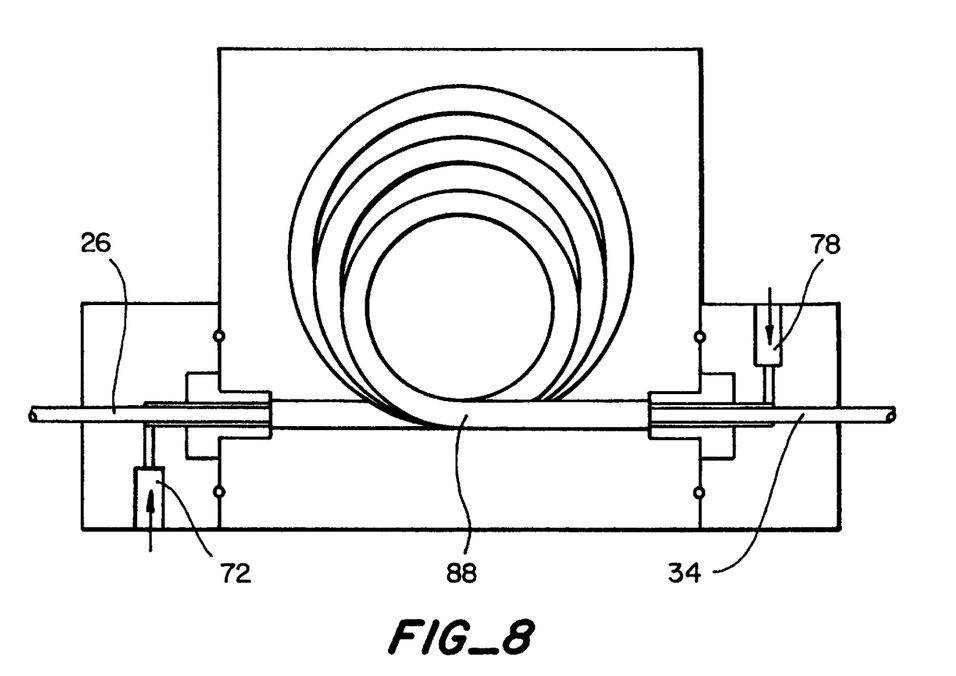
FIG. 8 is a schematic diagram of a liquid flow-through cell employing a looped light pipe.

The light pipe may be curved or looped to provide an increased light path length while minimizing the physical size. A liquid sample analyzing system employing a looped light pipe 88 is schematically shown in FIG. 8, wherein the same reference numbers as used for like parts of FIG. 4 have been applied. As described above, the input modes must be adjusted to minimize the RI.

There is provided a fiber-coupled analyzing system with a flow-through cell having a liquid waveguide or light pipe that can be located adjacent the analyte source away from the light source, optical components and signal processing electronics. A novel method and structure is taught for a high NA, liquid core, bufferless liquid flow-through cell that guides light by total internal reflection for determining the absorbance of an analyte used in high performance liquid chromatography (HPLC), capillary liquid chromatography (μLC), and capillary electrophoresis (CE), capillary electrochromatography (CEC), super critical liquid chromatography (SFC), flow injection analysis (FIA), and related techniques. The flow-through cell includes a light pipe that has high absorbance sensitivity, low scatter noise, high transmission efficiency, low RI sensitivity, low sensitivity to pressure changes and gas permeability, and is easily manufactured from extruded or preform pulled Teflon AF tubing. In one embodiment of the invention, the light pipe is optimized for higher order modes that increase absorbance sensitivity; has low RI sensitivity; has high transmission efficiency, low scatter noise; is relatively insensitive to temperature and pressure changes; operates over a large pressure range; has low sensitivity to pressure changes and gas permeability, and is easily manufactured from extruded or preform pulled Teflon AF tubing. In a further embodiment of the invention, fluorescence measurements may be taken since Teflon AF is highly transparent and nonscattering.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best use the invention, and various embodiments with various modifications as are suited to the particular use are contemplated. It is intended that the scope of the invention be defined by the claims appended hereto and their equivalents.

What is claimed is:

1. A fiber optic coupled light pipe for a liquid sample analyzer comprising:

a light pipe formed of a low refractive index material having a core diameter of predetermined size, an input optical fiber with a core diameter equal to or less than the core diameter of the light pipe core for introducing light into the light pipe, the end of said optical fiber being positioned relative to said light pipe so that light from the optical fiber core is accepted by the light pipe core, an output optical fiber with a core diameter equal to or greater than the core diameter to the light pipe core for receiving light from the input fiber transmitted along the light pipe, said input fiber having a numerical aperture less than or equal to the numerical aperture of the light pipe, said output fiber having a numerical aperture greater than or equal to the numerical aperture of the light pipe.

2. The light pipe as described in claim 1 in which the light pipe is made from Teflon AF.

3. The light pipe as described in claim 1, of such a thickness so as to withstand high pressures typically used in liquid chromatography and mass spectrometry.

4. The light pipe as described in claim 1 with an input fluid tubing that is in intimate thermal contact with the light pipe support body to rapidly thermally equilibrate the solution.

5. The light pipe as described in claim 1 where the annular alignment of the input and output optical fiber with respect to the input and output light pipe core is minimized to keep the RI below ±7 mAU.

6. The light pipe as described in claim 1 where the lateral alignment of the input and output optical fiber with respect to the input and output light pipe core is minimized to keep the RI below ±7 mAU.

7. The light pipe as described in claim 1 where a mode controller and/or mode scrambler is used to control the input light launch conditions to the input optical fiber so as to minimize the RI.

8. The light pipe as described in claim 1 where the output optical fiber is larger than the light pipe core during low and high pressure operation or when pressures change due to viscosity or temperature change the core diameter of the light pipe.

9. The light pipe as described in claim 1 where the bend radius of the light pipe is controlled so as so avoid optical losses that would create an RI greater than ±7 mAU.

10. In a liquid sample analyzing system including
a flow cell in the form of a light pipe of tubular construction having first and second ends,
first and second end caps sealed to said first and second ends of said light pipe,
an input passage formed in said first end cap spaced from the first end of the light pipe,
a multimode optical fiber extending into and sealed to said first end cap with its end optically coupled to said one end of said light pipe so that all fiber optic optical modes are captured by said light pipe to propagate therealong,
an annular space around the end of said multimode optical fiber extending between said input passage and the first end of said light pipe whereby input liquid flows around and along said end of said optical fiber into said light pipe to provide a smooth flow of liquid sample past the end of said fiber,
an output passage formed in said second end cap spaced from the second end of the light pipe,
an output optical fiber extending into and sealed to said second end cap with its end optically coupled to said second end of said light pipe so that all optical modes which propagate along said light pipe are captured by the optical fiber, and
the longitudinal alignment of the input and output optical fiber with respect to the input and output light pipe core is optimized to keep the RI below ±7 mAU, and
an annular space around the end of said output optical fiber between said output passage and the second end of said light pipe whereby liquid flowing from said light pipe flows around and along the end of said output optical fiber to provide a smooth flow of sample past the end of said output fiber.

11. In a liquid sample analyzing system including
a flow cell in the form of a light pipe of tubular construction having first and second ends,
first and second end caps sealed to said first and second ends of said light pipe,
an input passage formed in said first end cap spaced from the first end of the light pipe,
a multimode optical fiber extending into and compression sealed within said first end cap with its end optically coupled to said one end of said light pipe so that all fiber optic optical modes are captured by said light pipe to propagate therealong,
an annular space around the end of said multimode optical fiber extending between said input passage and the first end of said light pipe whereby input liquid flows around and along said end of said optical fiber into said light pipe to provide a smooth flow of liquid sample past the end of said fiber,
an output passage formed in said second end cap spaced from the second end of the light pipe,
an output optical fiber extending into and compression sealed within said second end cap with its end optically coupled to said second end of said light pipe so that all optical modes which propagate along said light pipe are captured by the optical fiber,
an annular space around the end of said output optical fiber between said output passage and the second end of said light pipe whereby liquid flowing from said light pipe flows around and along the end of said output optical fiber to provide a smooth flow of sample past the end of said output fiber.

12. A liquid sample analyzing system as in claim 11 where the optical fibers have a coating of Teflon AF that can serve as a gasket for the compression seal.

13. A liquid sample analyzing system as described in claim 11 where the coating of Teflon AF serves as protection against chemical attack.

14. A liquid sample analyzing system as described in claim 11 where the coating of Teflon AF serves as an antireflection coating.

15. A liquid sample analyzing system as described in claim 11 where higher order modes are caused to propagate to maximize the optical path length the light travels in the liquid in the light pipe so as to maximize the sensitivity of the light pipe.

16. In a liquid sample analyzing system including
a flow cell in the form of a light pipe of tubular construction having first and second ends, and disposed in a gas impermeable environment or container,
first and second end caps sealed to said first and second ends of said light pipe,
an input passage formed in said first end cap spaced from the first end of the light pipe,
a multimode optical fiber extending into and sealed to said first end cap with its end optically coupled to said one end of said light pipe so that all fiber optic optical modes are captured by said light pipe to propagate therealong,
an annular space around the end of said multimode optical fiber extending between said input passage and the first end of said light pipe whereby input liquid flows around and along said end of said optical fiber into said light pipe to provide a smooth flow of liquid sample past the end of said fiber,
an output passage formed in said second end cap spaced from the second end of the light pipe,
an output optical fiber extending into and sealed to said second end cap with its end optically coupled to said second end of said light pipe so that all optical modes which propagate along said light pipe are captured by the optical fiber,
an annular space around the end of said output optical fiber between said output passage and the second end of said light pipe whereby liquid flowing from said light pipe flows around and along the end of said output optical fiber to provide a smooth flow of sample past the end of said output fiber.

17. In a liquid sample analyzing system including
a flow cell in the form of a light pipe of tubular construction having first and second ends,
first and second end caps sealed to said first and second ends of said light pipe,
an input passage formed in said first end cap spaced from the first end of the light pipe,
a multimode optical fiber extending into and sealed to said first end cap with its end optically coupled to said one end of said light pipe so that all fiber optic optical modes are captured by said light pipe to propagate therealong, an annular space around the end of said multimode optical fiber extending between said input passage and the first end of said light pipe whereby input liquid flows around and along said end of said optical fiber into said light pipe to provide a smooth flow of liquid sample past the end of said fiber, an output passage formed in said second end cap spaced from the second end of the light pipe, an output optical fiber extending into and sealed to said second end cap with its end optically coupled to said second end of said light pipe so that all optical modes which propagate along said light pipe are captured by the optical fiber, where the inner diameter of the light pipe core is tapered with the larger diameter at the input optical fiber and the diameter of the taper at the output optical fiber is smaller than the output optical fiber, an annular space around the end of said output optical fiber between said output passage and the second end of said light pipe whereby liquid flowing from said light pipe flows around and along the end of said output optical fiber to provide a smooth flow of sample past the end of said output fiber.

18. In a liquid sample analyzing system including
a flow cell in the form of a light pipe of tubular construction and made of Teflon AF with an index of refraction less than 1.31, and having first and second ends, first and second end caps sealed to said first and second ends of said light pipe, an input passage formed in said first end cap spaced from the first end of the light pipe, a multimode optical fiber extending into and sealed to said first end cap with its end optically coupled to said one end of said light pipe so that all fiber optic optical modes are captured by said light pipe to propagate therealong, an annular space around the end of said multimode optical fiber extending between said input passage and the first end of said light pipe whereby input liquid flows around and along said end of said optical fiber into said light pipe to provide a smooth flow of liquid sample past the end of said fiber, an output passage formed in said second end cap spaced from the second end of the light pipe, an output optical fiber extending into and sealed to said second end cap with its end optically coupled to said second end of said light pipe so that all optical modes which propagate along said light pipe are captured by the optical fiber, an annular space around the end of said output optical fiber between said output passage and the second end of said light pipe whereby liquid flowing from said light pipe flows around and along the end of said output optical fiber to provide a smooth flow of sample past the end of said output fiber.

19. A liquid sample analyzer including
a light source,
means for introducing light from said light source into an optical cable,
a flow-through cell for receiving a sample to be analyzed, said flow-through cell including
  a light pipe formed of a low refractive index material having a core diameter of predetermined size coupled to said optical cable,
  said light pipe having an inner diameter equal to or greater than the diameter of the optical cable, the end of said optical cable being positioned relative to said light pipe so that refracted light from the optical cable is accepted by the light pipe core,
an output optical cable with a core diameter equal to or greater than the core diameter to the light pipe core for receiving light from the input fiber transmitted along the light pipe,
said input optical cable having a numerical aperture less than or equal to the numerical aperture of the light pipe,
said output optical cable having a numerical aperture greater than or equal to the numerical aperture of the light pipe,
means for receiving the light from said output optical cable and processing the light to obtain a measure of absorbance as a function of wavelength of the light transmitted through the light pipe.

20. The liquid sample analyzer of claim 19 in which the light pipe is made from Teflon AF.

21. The liquid sample analyzer of claim 19 of such a thickness so as to withstand high pressures typically used in liquid chromatography and mass spectrometry.

22. The liquid sample analyzer of claim 19 where the annular alignment of the input and output optical fiber with respect to the input and output light pipe core is minimized to keep the RI below ±7 mAU.

23. The liquid sample analyzer of claim 19 where the lateral alignment of the input and output optical fiber with respect to the input and output light pipe core is minimized to keep the RI below ±7 mAU.

24. The liquid sample analyzer of claim 19 where the longitudinal alignment of the input and output optical fiber with respect to the input and output light pipe core is optimized to keep the RI below ±7 mAU.

25. The liquid sample analyzer of claim 19 where a mode controller and/or mode scrambler is coupled to the optic cable to control the input light conditions to minimize the RI.

26. A liquid sample analyzing system as described in claim 19 where the inner diameter of the light pipe core is tapered with the larger diameter at the input optic cable and the diameter of the taper at the output optic cable is smaller than the output optical fiber.

27. A liquid sample analyzing system as described in claim 19 where higher order modes are caused to propagate to maximize the optical path length the light travels in the liquid in the light pipe so as to maximize the sensitivity of the light pipe.

28. A liquid sample analyzer as in claim 19 in which said means for receiving and processing the output of the output optic cable comprises a spectrometer for receiving the light and providing an output electrical signal and means for processing the electrical signal.

29. A liquid sample analyzer as in claim 19 in which a monochrometer processes the light in said input optic cable to sequentially provide light of different wavelengths to said light pipe and the light from said output optic cable is detected to generate electrical signals and the electrical signals are processed to provide a measure of absorbance of the sample as a function of wavelength.

* * * * *